(12) United States Patent
Hammond

(10) Patent No.: US 12,693,514 B2
(45) Date of Patent: Jul. 28, 2026

(54) METHODS AND SYSTEMS FOR VERIFYING BIOLOGICAL ANALYSIS DEVICES

(71) Applicant: IDEXX Laboratories, Inc., Westbrook, ME (US)

(72) Inventor: Jeremy Hammond, Standish, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 91 days.

(21) Appl. No.: 18/940,079

(22) Filed: Nov. 7, 2024

(65) Prior Publication Data

US 2025/0147298 A1    May 8, 2025

Related U.S. Application Data

(60) Provisional application No. 63/597,168, filed on Nov. 8, 2023.

(51) Int. Cl.
| | |
|---|---|
| *G02B 21/36* | (2006.01) |
| *G01N 21/64* | (2006.01) |
| *G16H 50/70* | (2018.01) |

(52) U.S. Cl.
CPC ....... *G02B 21/365* (2013.01); *G01N 21/6458* (2013.01); *G16H 50/70* (2018.01); *G01N 2201/127* (2013.01)

(58) Field of Classification Search
CPC ............. G02B 21/365; G01N 21/6458; G01N 2201/127; G16H 50/70
See application file for complete search history.

(56) References Cited

U.S. PATENT DOCUMENTS

| | | | | |
|---|---|---|---|---|
| 7,257,243 | B2 * | 8/2007 | Schmidt ............. | G01N 15/1468 |
| | | | | 382/128 |
| 2020/0103327 | A1 | 4/2020 | Florence et al. | |
| 2020/0249459 | A1 | 8/2020 | Eshel et al. | |
| 2020/0311465 | A1 | 10/2020 | Florence et al. | |

FOREIGN PATENT DOCUMENTS

WO    WO-2023186051 A1 *    10/2023    ............. G16H 50/20

OTHER PUBLICATIONS

International Search Report and Written Opinion issued in International Application No. PCT/US2024/055054.

* cited by examiner

*Primary Examiner* — Tony Ko

(74) *Attorney, Agent, or Firm* — Dinsmore & Shohl LLP

(57)    ABSTRACT

The present disclosure is directed to methods and systems for verifying biological analysis devices. The method includes calibrating a hematology device utilizing at least one of a quality control sample or historical patient data, generating diagnostic data associated with a portion of a biological sample with the hematology device, the diagnostic data comprising a first group of attributes associated with the biological sample, identifying whether the first group of attributes is within predetermined parameters, capturing an image of another portion of the biological sample with a microscopy device, identifying a second group of attributes associated with the biological sample based at least in part on the image, and determining one or more verification parameters based on the second group of attributes.

20 Claims, 4 Drawing Sheets

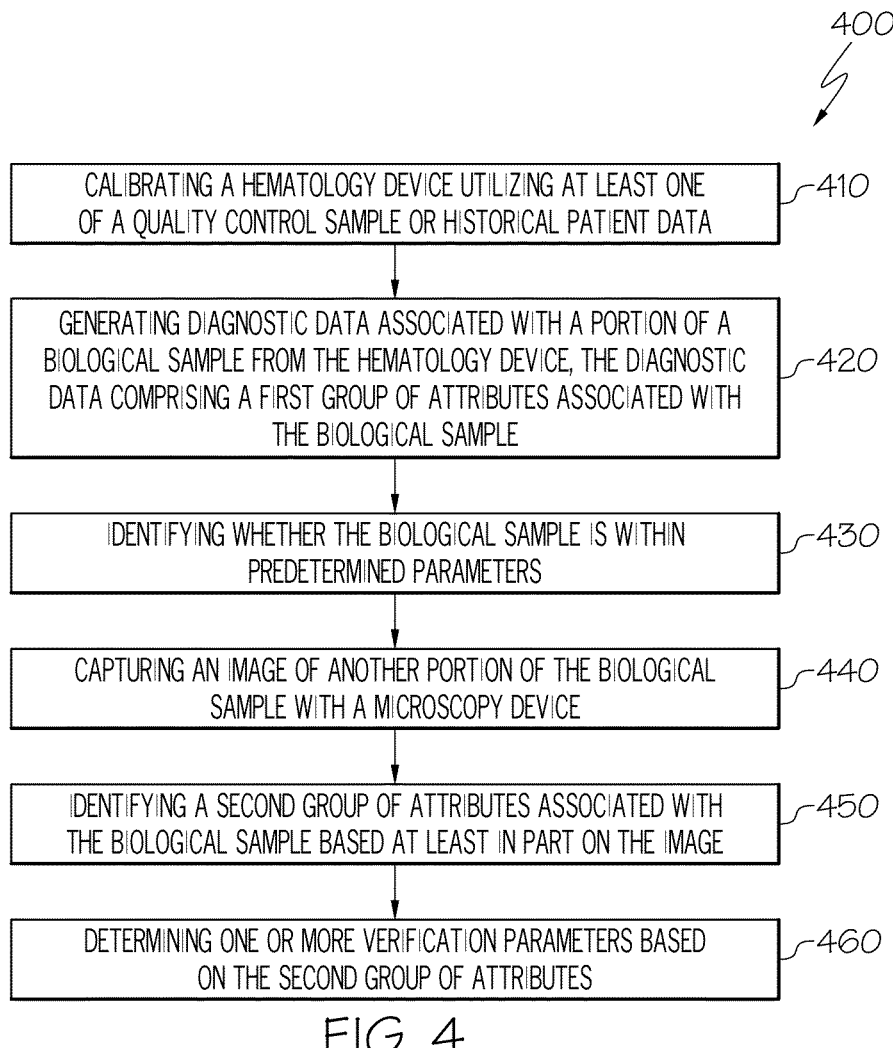

_400_

CALIBRATING A HEMATOLOGY DEVICE UTILIZING AT LEAST ONE OF A QUALITY CONTROL SAMPLE OR HISTORICAL PATIENT DATA — _410_

GENERATING DIAGNOSTIC DATA ASSOCIATED WITH A PORTION OF A BIOLOGICAL SAMPLE FROM THE HEMATOLOGY DEVICE, THE DIAGNOSTIC DATA COMPRISING A FIRST GROUP OF ATTRIBUTES ASSOCIATED WITH THE BIOLOGICAL SAMPLE — _420_

IDENTIFYING WHETHER THE BIOLOGICAL SAMPLE IS WITHIN PREDETERMINED PARAMETERS — _430_

CAPTURING AN IMAGE OF ANOTHER PORTION OF THE BIOLOGICAL SAMPLE WITH A MICROSCOPY DEVICE — _440_

IDENTIFYING A SECOND GROUP OF ATTRIBUTES ASSOCIATED WITH THE BIOLOGICAL SAMPLE BASED AT LEAST IN PART ON THE IMAGE — _450_

DETERMINING ONE OR MORE VERIFICATION PARAMETERS BASED ON THE SECOND GROUP OF ATTRIBUTES — _460_

FIG. 4

METHODS AND SYSTEMS FOR VERIFYING BIOLOGICAL ANALYSIS DEVICES

CROSS REFERENCE TO RELATED APPLICATION

This application claims priority to U.S. Provisional Patent Application Ser. No. 63/597,168, filed on Nov. 8, 2023, entitled "METHODS AND SYSTEMS FOR VERIFYING BIOLOGICAL ANALYSIS DEVICES," the entire contents of which are incorporated by reference in the present disclosure.

FIELD

The present disclosure relates to methods and systems for verifying biological analysis devices.

TECHNICAL BACKGROUND

Biological analysis devices, such as hematology devices and microscopy devices, may be used to analyze biological samples to check for abnormalities or information associated with the biological sample. Hematology devices may be used to analyze blood samples and may identify potential issues. Microscopy devices may be used to examine a variety of types of biological samples. To ensure the data produced by biological analysis devices is valid, the biological analysis devices should be verified, such as by testing or calibrating the biological analysis devices. Conventional biological analysis device verification methods and systems may involve the use of synthetic quality control samples and/or fixed cells to verify the biological analysis device is operating normally.

SUMMARY

Biological analysis devices may produce inaccurate information if the devices are not verified as calibrated and operating normally, which can lead to inaccurate diagnosis and undesirable health outcomes. To verify biological analysis devices, compiled historical patient data and/or quality control samples may be used, such as fixed cells or polymer beads. For example, in hematology devices such as flow cytometers and the like, polymer beads having known properties may be interrogated, and the results from the interrogation can be compared to expected results. Based on the comparison of the results to the expected results, one or more parameters of the hematology device can be corrected. A corresponding need exists for a biological analysis device verification method and system which may efficiently verify microscopy devices.

The present method and system can accurately and efficiently verify biological analysis devices by utilizing a quality control sample to verify a first device, then utilizing the verified first device to analyze a portion of a biological sample to verify the biological sample contains various parameters within predetermined thresholds, and then utilizing another portion of the same biological sample to verify a second biological analysis device.

In embodiments, the system generally includes a hematology device, a microscopy device, one or more processors, and a display. The hematology device and the microscopy device are configured to analyze a portion of a biological sample. The one or more processors may be configured to analyze and store detected attributes of the biological sample. The display may be configured to display the attributes detected by the hematology device and/or the microscopy device, a verification status of the hematology device and/or the microscopy device, or other types of information. The hematology device, the microscopy device, the one or more processors, and the display may be connected to one another via a network.

According to one embodiment, a method includes calibrating a hematology device utilizing at least one of a quality control sample or historical patient data, generating diagnostic data associated with a portion of a biological sample with the hematology device, the diagnostic data comprising a first group of attributes associated with the biological sample, identifying whether the first group of attributes is within predetermined parameters, capturing an image of another portion of the biological sample with a microscopy device, identifying a second group of attributes associated with the biological sample based at least in part on the image, and determining one or more verification parameters based on the second group of attributes.

According to another embodiment, a system includes a hematology device including a hematology processor and a non-transitory memory having stored therein instructions executable by the hematology processor to cause the hematology device to: calibrate the hematology device utilizing at least one of a quality control sample or historical patient data, generate diagnostic data associated with a portion of a biological sample, the diagnostic data comprising a first group of attributes associated with the biological sample, and identify whether the first group of attributes is within predetermined parameters; and a microscopy device communicatively coupled to the hematology device and comprising a microscopy processor and a non-transitory memory having stored therein instructions executable by the microscopy processor to: capture an image of another portion of the biological sample with the microscopy device, identify a second group of attributes associated with the biological sample, and determine one or more control parameters of the microscopy device based on the second group of attributes.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of the present disclosure may be better understood when read in conjunction with the following drawings in which:

FIG. 4 schematically depicts a flowchart of a method according to one or more embodiments shown and described herein.

Reference will now be made in greater detail to various embodiments of the present disclosure, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to methods and systems for calibrating biological analysis devices. The systems may include a hematology device, a microscopy device, one or more processors, and a display. In embodiments, the hematology device and the microscopy device are configured to analyze biological samples. The hematology device may be calibrated with a quality control sample, such as with a synthetic quality control sample. The calibrated hematology device may analyze a portion of a biological sample to determine one or more attributes associated with the biological sample. The system may determine if the attributes of the biological sample fall within predetermined parameters. The microscopy device may analyze another portion of the same biological sample. The system may determine a second set of attributes of the biological sample. The system may compare the first set of attributes to the second set of attributes, in order to verify the microscopy device. In some embodiments, the system compares the second set of attributes to predetermined attributes.

Conventional biological analysis verification systems may require verification of the biological analysis devices using compiled historical patient data, or quality control materials, such as fixed cells or synthetic quality control materials. However, microscopy devices lack sophisticated verification systems. The present system can efficiently verify microscopy devices by verifying one biological analysis device utilizing quality control materials or compiled historical patient data, and then use the verified biological analysis device to verify subsequent biological analysis devices, e.g., microscopy devices.

Figure 1:
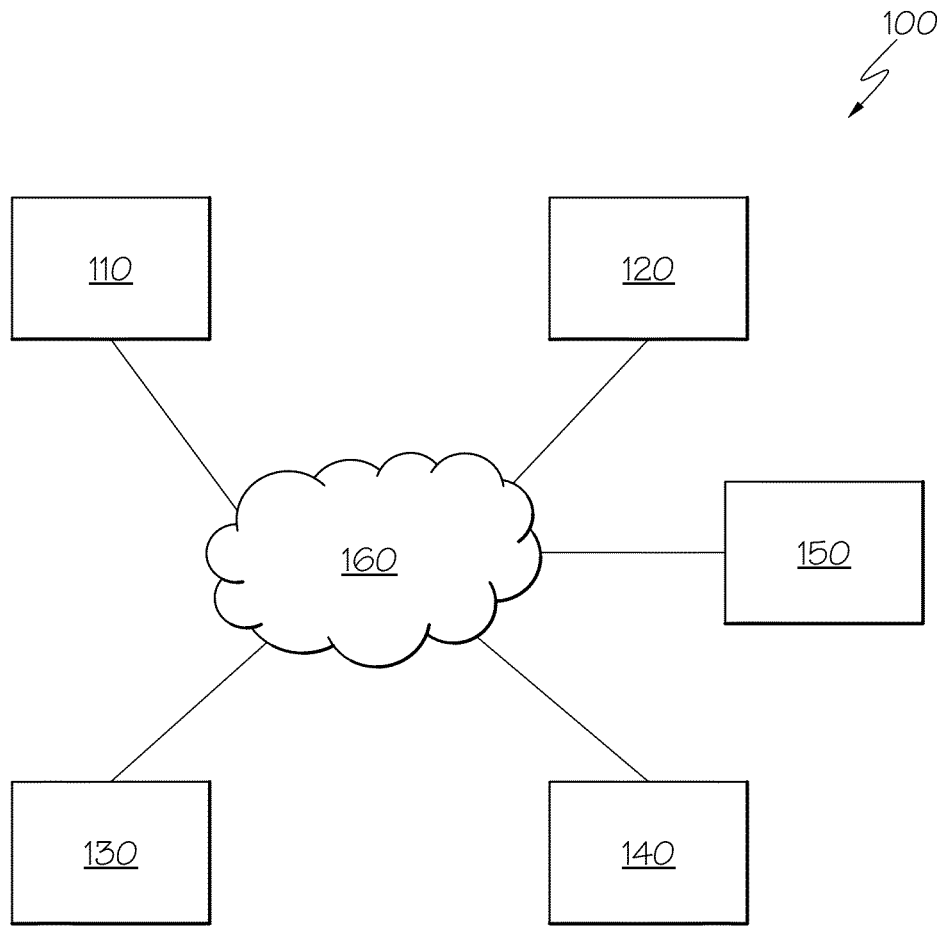
FIG. 1 schematically depicts a network of devices for performing a method, according to one or more embodiments shown and described herein.

Referring now to FIG. 1, an example of a system 100 for verifying biological analysis devices is shown consistent with a disclosed embodiment. As shown in FIG. 1, a hematology device 110, a microscopy device 120, a first processor 130, a second processor 140, and a display 150 are communicatively coupled to one another via a network 160. Although a specific numbers of hematology devices, microscopy devices, first processors, second processors, networks, and displays are depicted in FIG. 1, any number of these devices may be provided. Furthermore, the computing functions performed by one or more devices of system 100 may be combined and the functionality of any one or more components of system 100 may be implemented by any appropriate computing environment.

Network 160 facilitates communications between the various devices in system 100, such as the hematology device 110, the microscopy device 120, the first processor 130, the second processor 140, and the display 150. Network 160 may be a shared, public, or private network, may encompass a wide area or local area, and may be implemented through any suitable combination of wired and/or wireless communication networks. Furthermore, network 160 may include a local area network (LAN), a wide area network (WAN), an intranet, or the Internet. The network 160 may allow for near-real time communication between devices connected over the network.

The hematology device 110 and the microscopy device 120 may be configured to analyze biological samples. In embodiments, the hematology device 110 and the microscopy device 120 may analyze the biological sample to generate data reflective of attributes of the biological sample. The biological sample may be a sample of cells of a biological material, such as a blood sample or the like. In some embodiments the biological sample is taken from a primate, such as a human. In some embodiments, the biological sample is from a non-human animal, such as a cat, a dog, or any other non-human animal.

The hematology device 110 may analyze various attributes of the biological sample. In embodiments, the hematology device 110 may analyze a total cell count, a white blood cell count, a red blood cell count, a reticulocytes count, a platelets count, a neutrophils count, a lymphocytes count, a monocytes count, a eosinophils count, a mean corpuscular volume, a mean platelets volume, a red blood cell distribution width, a platelet distribution width, or any other suitable attributes of the biological sample. The hematology device 110 may have one or more parameters which are configured to be adjusted. In some embodiments, the parameters may be automatically adjusted. In some embodiments, the parameters may be manually adjusted. In embodiments, an optical density, a flow rate, an extinction channel, a low angle forward light scatter channel, a right angle scatter channel, a high angle forward light scatter channel, an impedance value, a fluorescent flow cytometry, a fluorescence peak position, and/or a time-of-flight channel of the hematology device 110 may be adjusted.

The microscopy device 120 may analyze various attributes of the biological sample. In embodiments, the microscopy device 120 may analyze quantitative or qualitative cellular features, or any other suitable attributes of the biological sample. The microscopy device 120 may have one or more parameters which are configured to be adjusted. In embodiments, an intensity of a light emitting device of the microscopy device 120 may be adjusted. In some embodiments, a duration of exposure of a camera shutter of the microscopy device 120 may be adjusted. In some embodiments, a magnification of a magnification device of the microscopy device 120 may be adjusted. In some embodiments, a focus-offset value of the microscopy device 120 may be adjusted. In some embodiments, a cleanliness of a vision portion of the microscopy device 120 may be determined, and if the microscopy device 120 is determined to be dirty, an alert may be provided to the user.

The first processor 130 may include a non-transitory, processor-readable storage medium for storing program modules that, when executed by the first processor 130, perform one or more processes described herein. Non-transitory, processor-readable storage medium may store data from devices, such as the hematology device 110 and/or the microscopy device 120. Non-transitory, processor-readable storage medium may be one or more memory devices that store data as well as software and may also comprise, for example, one or more of RAM, ROM, magnetic storage, or optical storage. Since disclosed embodiments may be implemented using an HTTPS (hypertext transfer protocol secure) environment, data transfer over a network, such as the Internet, may be done in a secure fashion.

In embodiments, the one or more program modules stored on the first processor 130 may include instructions to calibrate the hematology device 110, generate diagnostic data associated with a portion of the biological sample, and identify whether the biological sample is within predetermined parameters. In further embodiments, the one or more program modules may include instructions to complete any other suitable tasks.

The second processor 140 may include a non-transitory, processor-readable storage medium for storing program modules that, when executed by the second processor 140, perform one or more processes described herein. Non-transitory, processor-readable storage medium may store data from devices, such as the hematology device 110 and/or the microscopy device 120. Non-transitory, processor-readable storage medium may be one or more memory devices that store data as well as software and may also comprise, for example, one or more of RAM, ROM, magnetic storage, or optical storage. Since disclosed embodiments may be implemented using an HTTPS (hypertext transfer protocol secure) environment, data transfer over a network, such as the Internet, may be done in a secure fashion.

In embodiments, the one or more program modules stored on the second processor 140 may include instructions to capture an image of another portion of the biological sample, identify a second group of attributes associated with the biological sample, and determine one or more control parameters of the microscopy device 220. In some embodiments, the one or more program modules may include instructions to complete any other suitable tasks.

In embodiments, the display 150 is a screen, graphical user interface (GUI), or the like used to display information generated by the hematology device 110, the microscopy device 120, and/or other devices communicatively coupled to the display 150. In some embodiments, the display 150 may include one or more status lights for displaying a status of the hematology device 110 and/or the microscopy device 120. As a non-limiting example, the display 150 may display a calibration status of the hematology device 110 and/or the microscopy device 120, the date and time of the last verification of the hematology device 110 and/or the microscopy device 120, information associated with an analyzed biological sample, or other types of information. In embodiments, the display 150 may display a fluorescence, a saturation, a blood cell count from the hematology device 110, and/or a light intensity of the biological sample.

In some embodiments, the display 150 may be mechanically coupled to or integral with the hematology device 110 and/or the microscopy device 120. In some embodiments, the display 150 may be a standalone item communicatively coupled to the hematology device 110 and/or the microscopy device 120.

In some embodiments, the hematology device 110 and the microscopy device 120 may not be communicatively coupled to one another via network 160. As a non-limiting example, each of the hematology device 110 and the microscopy device 120 may have a display communicatively coupled thereto. An operator may manually observe attributes generated by each of the hematology device 110 and the microscopy device 120 by reading the information displayed on each of the displays 150. The operator may then determine if the hematology device 110 and/or the microscopy device 120 have been calibrated.

Figure 2:
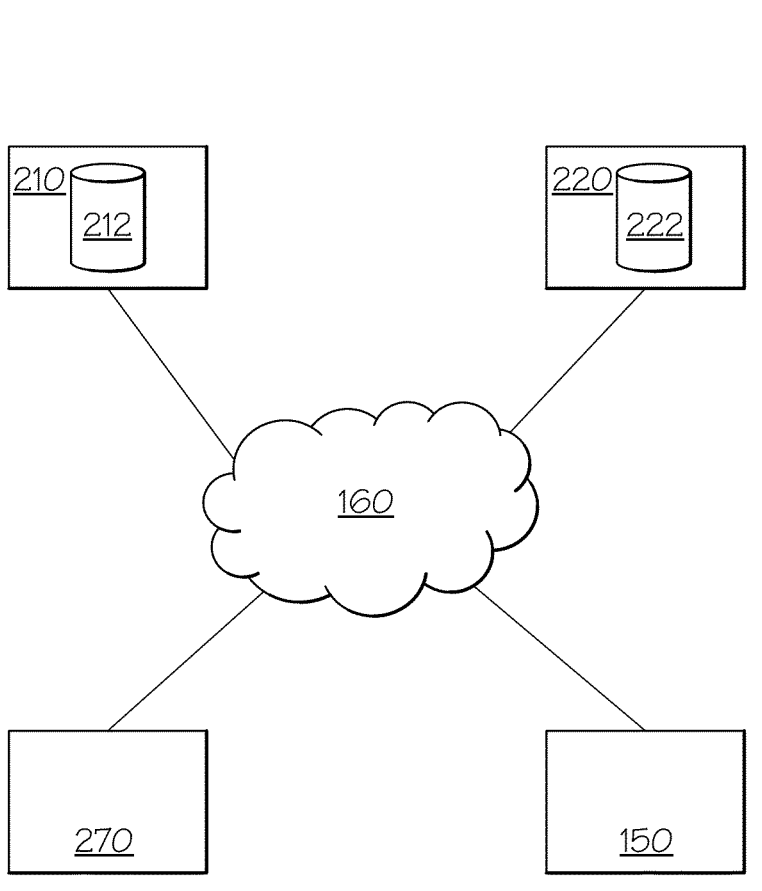
FIG. 2 schematically depicts a system made up of a network of devices, according to one or more embodiments shown and described herein.

Referring now to FIG. 2, an illustration of a system 200 for calibrating biological analysis devices is shown consistent with a disclosed embodiment. As shown in FIG. 2, a hematology device 210, a microscopy device 220, the display 150, and a central controller 270 are communicatively coupled to one another via the network 160. Although a specific numbers of hematology devices, microscopy devices, displays, networks, and central controllers are depicted in FIG. 2, any number of these devices may be provided. Furthermore, the computing functions performed by one or more devices of the system 200 may be combined and the functionality of any one or more components of system 200 may be implemented by any appropriate computing environment.

The hematology device 210 may include a hematology processor 212. The hematology processor 212 may include a non-transitory, processor-readable storage medium for storing program modules that, when executed by the hematology processor 212, perform one or more processes described herein. Non-transitory, processor-readable storage medium may store data from other devices, such as the central controller 270 and the microscopy device 220. Non-transitory, processor-readable storage medium may be one or more memory devices that store data as well as software and may also comprise, for example, one or more of RAM, ROM, magnetic storage, or optical storage. Since disclosed embodiments may be implemented using an HTTPS (hypertext transfer protocol secure) environment, data transfer over a network, such as the Internet, may be done in a secure fashion.

In embodiments, the one or more program modules stored on the hematology processor 212 may include instructions to calibrate the hematology device 210, generate diagnostic data associated with a portion of the biological sample, and identify whether the biological sample is within predetermined parameters. In further embodiments, the one or more program modules may include instructions to complete any other suitable tasks.

The microscopy device 220 may include a microscopy processor 222. The microscopy processor 222 may include a non-transitory, processor-readable storage medium for storing program modules that, when executed by the microscopy processor 222, perform one or more processes described herein. Non-transitory, processor-readable storage medium may store data from other devices, such as the central controller 270 and the hematology device 210. Non-transitory, processor-readable storage medium may be one or more memory devices that store data as well as software and may also comprise, for example, one or more of RAM, ROM, magnetic storage, or optical storage. Since disclosed embodiments may be implemented using an HTTPS (hypertext transfer protocol secure) environment, data transfer over a network, such as the Internet, may be done in a secure fashion.

In embodiments, the one or more program modules stored on the microscopy processor 222 may include instructions to capture an image of another portion of the biological sample, identify a second group of attributes associated with the biological sample, and determine one or more control parameters of the microscopy device 220. In some embodiments, the one or more program modules may include instructions to complete any other suitable tasks.

The central controller 270 may be a computing device configured to analyze the first group of attributes identified by the hematology device 210 and the second group of attributes identified by the microscopy device 220. In embodiments, the central controller 270 may be any suitable computing device, including but not limited to a programmable logic controller, a proportional controller, an integral controller, a derivative controller, or any other suitable type of controller. The central controller 270 may include a central processor.

Figure 3:
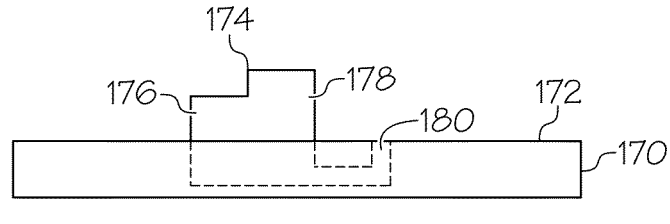
FIG. 3 schematically depicts a side view of a carrier for holding a biological sample, according to one or more embodiments shown and described herein.

Referring now to FIG. 3, an embodiment of a carrier 170 is illustrated consistent with a disclosed embodiment. The carrier 170 may be configured to hold a portion of the biological sample so that the biological sample may be analyzed. In embodiments, the microscopy device 220 is configured to hold the carrier 170. By holding the carrier 170, the microscopy device 220 images and interrogates the portion of the biological sample held within the carrier 170.

The carrier 170 may have an upper face 172 and a sample collection area 174 arranged on the upper face 172 of the carrier 170. The sample collection area 174 may be constructed of a transparent or translucent material such as glass or plastic so as to allow the biological sample to be viewed and analyzed when it is disposed therein. The biological sample may be injected into the sample collection area 174 through an injection port 180 (shown in phantom), which may be fluidly coupled to the sample collection area 174. The sample collection area 174 may have a plurality of sample holding areas. As illustrated, the sample collection area 174 has a first sample holding area 178 and a second sample holding area 176. The first sample holding area 178 may have a greater depth than the second sample holding area 176, such that the first sample holding area 178 extends a greater distance away from the upper face 172 of the carrier 170 than the second sample holding area 176. The multiple depths of the sample collection area 174 may allow a biological analysis device to detect certain attributes of the biological sample when the biological sample is captured at a first depth that may not be detectable when the biological sample is detected at a second depth, or vice-versa. The multiple depths of the sample collection area 174 may support effective dilution and/or concentration of the biological sample within the first sample holding area 178 and the second sample holding area 176.

While two depths of sample holding areas are shown, it should be understood that in embodiments, any number of depths of sample holding areas may be used, such as one depth, three depths, five depths, or any other suitable number of depths. While the carrier 170 is described and depicted as having sample holding areas 176, 178 for holding liquid samples, it should be understood that the carrier 170 may include any suitable device for interrogating a blood sample, such as a blood slide or the like. In some embodiments, the carrier 170 may wholly or partially encapsulate the biological sample.

Referring now to FIG. 4, an illustration of a method 400 is illustrated with reference to FIGS. 1-3 consistent with a disclosed embodiment. The method 400 is directed at calibrating biological analysis devices. At step 410, the method 400 includes calibrating a hematology device with at least one of a quality control sample or historical patient data. That is, the hematology device 110 or the hematology device 210 may be verified with quality control sample parameters or historical patient data. If the hematology device 110 or the hematology device 210 is calibrated by the quality control sample, the system 100 or the system 200 may determine that the hematology device 110 or the hematology device 210 is operating normally and may be used to calibrate the microscopy device 120 or the microscopy device 220.

At step 420, the method 400 includes generating diagnostic data associated with a portion of the biological sample from the hematology device, the diagnostic data comprising a first group of attributes associated with the biological sample. That is, the hematology device 110 or the hematology device 210 may analyze a portion of the biological sample. In some embodiments, the portion of the biological sample may be loaded onto the carrier 170 to be held and analyzed by the hematology device 110 or the hematology device 210. The hematology device 110 or the hematology device 210 may generate diagnostic data corresponding to certain attributes of the portion of the biological sample, including but not limited to a total cell count, a white blood cell count, a red blood cell count, a reticulocytes count, a platelets count, a neutrophils count, a lymphocytes count, a monocytes count, a eosinophils count, a mean corpuscular volume, a mean platelets volume, a red blood cell distribution width, a platelet distribution width, or any other suitable attributes of the biological sample.

At step 430, the method 400 includes identifying whether the biological sample is within predetermined parameters. That is, the first processor 130 or the hematology processor 212 may compare the diagnostic data associated with the biological sample and generated by the hematology device 110 or the hematology device 210 to the predetermined parameters to determine if the biological sample falls within the predetermined parameters. If the biological sample is identified to be within the predetermined parameters, the system 100 may determine that the biological sample may be used to calibrate the microscopy device 120 or the microscopy device 220.

At step 440, the method 400 includes capturing an image of another portion of the biological sample from a microscopy device. That is, another portion of the biological sample may be held by the microscopy device 120 or the microscopy device 220 so that the microscopy device 120 or the microscopy device 220 may capture an image or series of images of biological sample. The biological sample imaged by the microscopy device 120 or the microscopy device 220 is a different portion from the same biological sample that is analyzed by the hematology device 110 or the hematology device 210. That is, the biological sample may be divided into two or more portions, such that a first portion of the biological sample is analyzed by the hematology device 110 or the hematology device 210 and a second portion of the biological sample is analyzed by the microscopy device 120 or the microscopy device 220. In embodiments, the second portion of the biological sample may be loaded onto the same carrier 170 as was used in step 410 after the carrier has been cleaned. In further embodiments, the second portion of the biological sample may be loaded onto a second carrier 170.

At step 450, the method 400 includes identifying a second group of attributes associated with the biological sample. That is, the second processor 140 or the microscopy processor 222 may identify a second group of attributes associated with the second portion of the biological sample. The second group of attributes may correspond to the first group of attributes, so that the first group of attributes may be directly compared to the second group of attributes.

At step 460, the method 400 includes determining one or more verification parameters based on the second group of attributes. That is, the system 100 or the system 200 may compare the first group of attributes and the second group of attributes. If the first group of attributes and the second group of attributes match, or are within a predetermined range of one another, the system 100 or the system 200 may determine that all of the verification parameters associated with the microscopy device 120 or the microscopy device 220 have been calibrated. The verification parameters may include but not be limited to the operation of a light emitting device of the microscopy device 120 or the microscopy device 220, the operation of a duration of exposure of a camera shutter of the microscopy device 120 or the microscopy device 220, and/or the operation of a magnification of the magnification device of the microscopy device 120 or the microscopy device 220. In other embodiments, the verification parameters may include other suitable parts or systems of the microscopy device 120 or the microscopy device 220.

Figure 5:
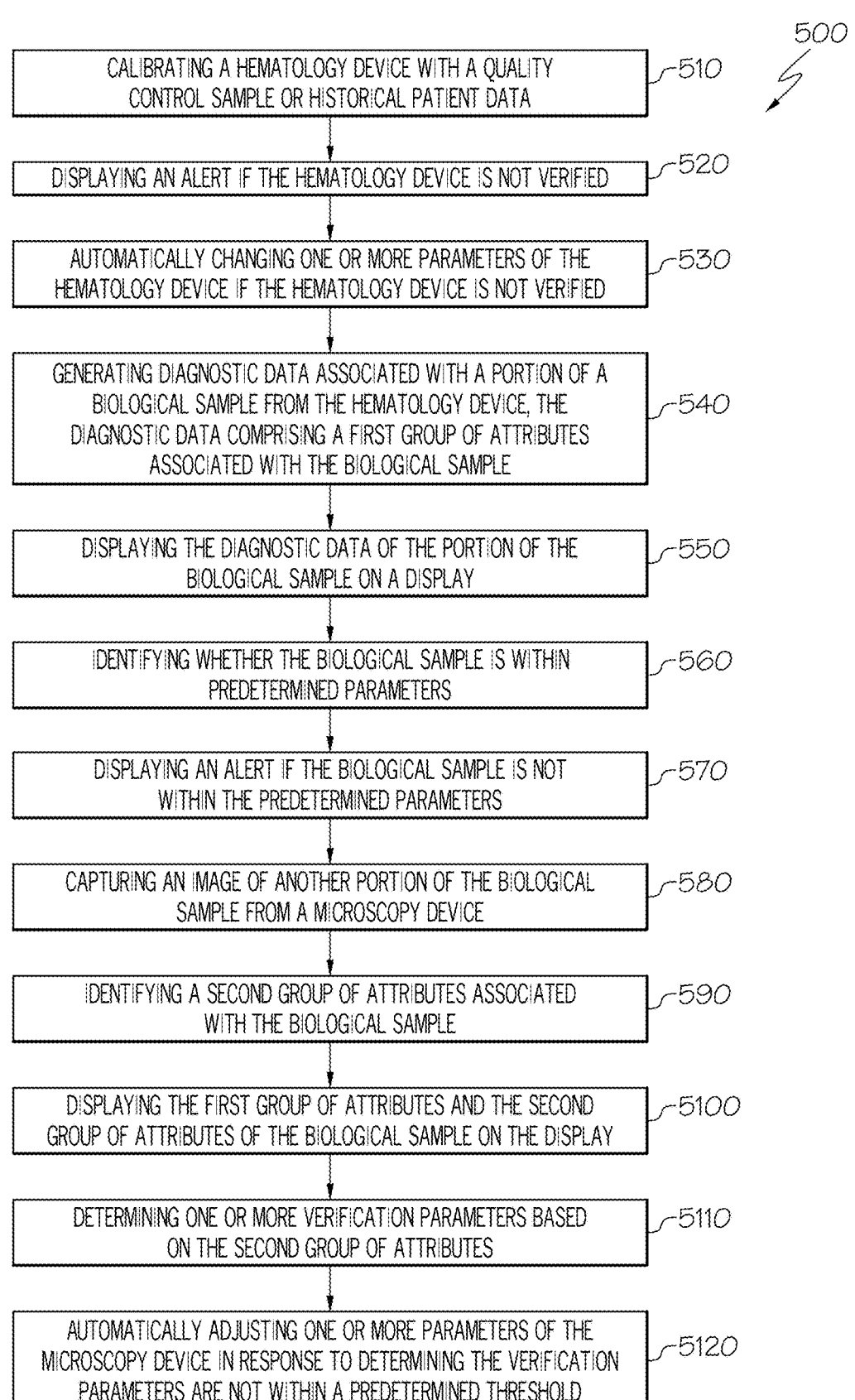
FIG. 5 schematically depicts a flowchart of a method according to one or more embodiments shown and described herein.

Referring now to FIG. 5, an illustration of a method 500 is illustrated with reference to FIGS. 1-3 consistent with a disclosed embodiment. The method 500 is directed at calibrating biological analysis devices. At step 510, the method 500 includes calibrating a hematology device with a quality control sample. That is, the hematology device 110 or the hematology device 210 may be calibrated with a quality control sample or historical patient data. If the hematology device 110 or the hematology device 210 is verified by the quality control sample or historical patient data, the system 100 or the system 200 may determine that the hematology device 110 or the hematology device 210 is operating normally and may be used to verify the microscopy device 120 or the microscopy device 220.

At step 520, the method 500 includes displaying an alert if the hematology device 110 or the hematology device 210 is not verified. That is, the first processor 130 or the hematology processor 212 may display an alert to notify the user that the hematology device 110 or the hematology device 210 is not verified. In embodiments, the alert may include activating a light, activating a buzzer, generating a sound, or any other suitable way for alerting the user.

At step 530, the method 500 includes automatically changing one or more parameters of the hematology device 110 or the hematology device 210 if the hematology device 110 or the hematology device 210 is not verified. That is, the first processor 130 or the hematology processor 212 may adjust an optical density of the hematology device 110 or the hematology device 210, a flow rate of the hematology device 110 or the hematology device 210, an extinction channel of the hematology device 110 or the hematology device 210, a low angle forward light scatter channel of the hematology device 110 or the hematology device 210, a right angle scatter channel of the hematology device 110 or the hematology device 210, a high angle forward light scatter channel of the hematology device 110 or the hematology device 210, a time-of-flight channel of the hematology device 110 or the hematology device 210, a fluorescence peak positon of the hematology device 110 or the hematology device 210, or any other suitable parameters of the hematology device 110 or the hematology device 210.

At step 540, the method 500 includes generating diagnostic data associated with a portion of the biological sample from the hematology device 110 or the hematology device 210, the diagnostic data comprising a first group of attributes associated with the biological sample. That is, the hematology device 110 or the hematology device 210 may analyze a portion of the biological sample. In some embodiments, the portion of the biological sample may be loaded onto the carrier 170 to be held and analyzed by the hematology device 110 or the hematology device 210. The hematology device 110 or the hematology device 210 may generate diagnostic data corresponding to certain attributes of the portion of the biological sample, including but not limited to a total cell count, a white blood cell count, a red blood cell count, a reticulocytes count, a platelets count, a neutrophils count, a lymphocytes count, a monocytes count, a eosinophils count, a mean corpuscular volume, a mean platelets volume, a red blood cell distribution width, a platelet distribution width, or any other suitable attributes of the biological sample.

At step 550, the method 500 includes displaying the diagnostic data of the portion of the biological sample on the display 150. That is, the diagnostic data may be displayed on the display 150 so that the user may observe the diagnostic data.

At step 560, the method 500 includes identifying whether the biological sample is within a predetermined range. That is, the first processor 130 or the hematology processor 212 may compare the diagnostic data associated with the biological sample and generated by the hematology device 110 or the hematology device 210 to the predetermined range to determine if the biological sample falls within the predetermined range. If the biological sample is identified to be within the predetermined range the system 100 may determine that the biological sample may be used to verify the microscopy device 120 or the microscopy device 220.

At step 570, the method 500 includes displaying an alert if the biological sample is not within predetermined parameters. That is, the first processor 130 or the hematology processor 212 may generate an alert to notify the user that the biological sample is not within predetermined parameters. In embodiments, the alert may include activating a light, activating a buzzer, generating a sound, or any other suitable way for alerting the user.

At step 580, the method 500 includes receiving an image of another portion of the biological sample from a microscopy device. That is, another portion of the biological sample may be held by the microscopy device 120 or the microscopy device 220 so that the microscopy device 120 or the microscopy device 220 may capture an image of biological sample. The biological sample imaged by the microscopy device 120 or the microscopy device 220 is a different portion from the same biological sample that is analyzed by the hematology device 110 or the hematology device 210. That is, the biological sample may be divided into two or more portions, such that a first portion of the biological sample is analyzed by the hematology device 110 or the hematology device 210 and a second portion of the biological sample is analyzed by the microscopy device 120 or the microscopy device 220. In embodiments, the second portion of the biological sample may be loaded onto the same carrier 170 as was used in step 510 after the carrier 170 has been cleaned. In further embodiments, the second portion of the biological sample may be loaded onto a second carrier 170.

At step 590, the method 500 includes identifying, by a processor, a second group of attributes associated with the biological sample. That is, the second processor 140 or the microscopy processor 222 may identify a second group of attributes associated with the second portion of the biological sample. The second group of attributes may correspond to the first group of attributes, so that the first group of attributes may be directly compared to the second group of attributes.

At step 5100, the method 500 includes displaying the first group of attributes and the second group of attributes of the biological sample on the display 150. That is, the first group of attributes and the second group of attributes of the biological sample may be displayed on the display 150 so that the user may observe and compare the first group of attributes and the second group of attributes.

At step 5110, the method 500 includes determining one or more verification parameters based on the first group of attributes and the second group of attributes. That is, the system 100 or the system 200 may compare the first group of attributes and the second group of attributes. If the first group of attributes and the second group of attributes match, or are within a predetermined range of one another, the system 100 or the system 200 may determine that all of the verification parameters associated with the microscopy device 120 or the microscopy device 220 have been verified. The verification parameters may include but not be limited to the operation of a light emitting device of the microscopy device 120 or the microscopy device 220, the operation of a duration of exposure of a camera shutter of the microscopy device 120 or the microscopy device 220, and/or the operation of a magnification of the magnification device of the microscopy device 120 or the microscopy device 220. In other embodiments, the verification parameters may include other suitable parts or systems of the microscopy device 120 or the microscopy device 220.

At step 5120, the method 500 includes automatically adjusting one or more parameters of the microscopy device 120 or the microscopy device 220 in response to determining the verification parameters are not within a predetermined threshold. That is, the second processor 140 or the microscopy processor 222 may adjust an intensity of a light emitting device of the microscopy device 120 or the microscopy device 220, a duration of exposure of a camera shutter of the microscopy device 120 or the microscopy device 220, a magnification of a magnification device of the microscopy device 120 or the microscopy device 220, or any other suitable parameters of the microscopy device 120 or the microscopy device 220.

Accordingly embodiments of the present disclosure provide a methods and systems for verifying biological analysis devices. The methods and systems may include a hematology device, a microscopy device, one or more processors, and a display. The hematology device and the microscopy device may be configured to analyze biological samples. The hematology device may be verified with a quality control sample, such as with a synthetic biological sample. The verified hematology device may analyze a portion of a biological sample to determine one or more attributes associated with the biological sample. The system may determine if the attributes of the biological sample fall within predetermined parameters. The microscopy device may analyze another portion of the biological sample. The system may determine a second set of attributes of the biological sample. The system may compare the first set of attributes to the second set of attributes, in order to verify the microscopy device.

It may be noted that one or more of the following claims utilize the terms "where," "wherein," or "in which" as transitional phrases. For the purposes of defining the present technology, it may be noted that these terms are introduced in the claims as an open-ended transitional phrase that are used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it may be noted that the various details described in this disclosure should not be taken to imply that these details relate to elements that are essential components of the various embodiments described in this disclosure, even in casings where a particular element may be illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

The invention claimed is:

1. A method comprising:

calibrating a hematology device utilizing at least one of a quality control sample or historical patient data;

generating diagnostic data associated with a portion of a biological sample with the hematology device, the diagnostic data comprising a first group of attributes associated with the biological sample;

identifying whether the first group of attributes is within predetermined parameters;

capturing an image of another portion of the biological sample with a microscopy device;

identifying a second group of attributes associated with the biological sample based at least in part on the image; and determining one or more verification parameters based on the second group of attributes.

2. The method of claim 1, further comprising, in response to identifying that the first group of attributes is within the predetermined parameters, generating a display indicating that the biological sample is suitable for calibrating the microscopy device.

3. The method of claim 1, wherein the biological sample is a blood sample.

4. The method of claim 1, wherein calibrating the hematology device utilizing the at least one of the quality control sample or the historical patient data comprises:

interrogating the quality control sample;

determining quality control sample parameters based on the interrogating of the quality control sample;

determining whether the quality control parameters are within a predetermined threshold; and in response to determining that the quality control parameters are not within the predetermined threshold, changing one or more parameters of the hematology device.

5. The method of claim 4, wherein changing the one or more parameters of the hematology device includes changing one or more of an optical density of the hematology device, a flow rate of the hematology device, an extinction channel of the hematology device, a low angle forward light scatter channel of the hematology device, a right angle scatter channel of the hematology device, a high angle forward light scatter channel of the hematology device, fluorescence, calibration factors, and a time-of-flight channel of the hematology device.

6. The method of claim 1, further comprising changing one or more parameters of the microscopy device in response to determining the verification parameters are not within a predetermined threshold.

7. The method of claim 6, wherein changing the one or more parameters includes changing one or more of an intensity of a light emitting device of the microscopy device, a duration of exposure of a camera shutter of the microscopy device, focus parameters, and a magnification of a magnification device of the microscopy device.

8. The method of claim 1, wherein capturing the image of another portion of the biological sample comprises capturing an image the biological sample on a carrier.

9. The method of claim 8, wherein the biological sample is at least partially encapsulated within the carrier.

10. The method of claim 8, wherein the carrier comprises a first sample holding area and a second sample holding area, and wherein the first sample holding area has a greater depth than the second sample holding area.

11. The method of claim 1, further comprising displaying an alert if the verification parameters are not within a predetermined threshold.

12. The method of claim 1, further comprising displaying on a display the first group of attributes of the biological sample and the second group of attributes of the biological sample.

13. A system comprising:

a hematology device comprising a hematology processor and a non-transitory memory having stored therein instructions executable by the hematology processor to cause the hematology device to:

calibrate the hematology device utilizing at least one of a quality control sample or historical patient data;

generate diagnostic data associated with a portion of a biological sample, the diagnostic data comprising a first group of attributes associated with the biological sample; and identify whether the first group of attributes is within predetermined parameters; and a microscopy device communicatively coupled to the hematology device and comprising a microscopy processor and a non-transitory memory having stored therein instructions executable by the microscopy processor to:

capture an image of another portion of the biological sample with the microscopy device;

identify a second group of attributes associated with the biological sample; and determine one or more control parameters of the microscopy device based on the second group of attributes.

14. The system of claim 13, further comprising a central controller, wherein the central controller is communicatively coupled to the hematology device and the microscopy device, the central controller comprising a central processor and a non-transitory memory having stored therein instructions executable by the central processor to compare the first group of attributes and the second group of attributes.

15. The system of claim 13, wherein the microscopy device is configured to hold a carrier with the biological sample.

16. The system of claim 15, wherein the carrier at least partially encapsulates the biological sample.

17. The system of claim 13, wherein the instructions executable by the hematology processor to cause the hematology device to calibrate the hematology device utilizing the at least one of the quality control sample or the historical patient data by:

interrogating the quality control sample;

determining quality control sample parameters based on the interrogating of the quality control sample;

determining whether the quality control parameters are within a predetermined threshold; and in response to determining that the quality control parameters are not within the predetermined threshold, changing one or more parameters of the hematology device.

18. The system of claim 17, wherein changing the one or more parameters of the hematology device includes changing at least one of an optical density of the hematology device, a flow rate of the hematology device, an extinction channel of the hematology device, a low angle forward light scatter channel of the hematology device, a right angle scatter channel of the hematology device, a high angle forward light scatter channel of the hematology device, and a time-of-flight channel of the hematology device.

19. The system of claim 13, wherein the microscopy processor is configured to automatically adjust one or more parameters of the microscopy device if the quality control parameters are not within a predetermined threshold.

20. The system of claim 19, wherein automatically adjust one or more parameters includes adjusting at least one of an intensity of a light emitting device of the microscopy device, a duration of exposure of a camera shutter of the microscopy device, and a magnification of a magnification device of the microscopy device.

* * * * *